United States Patent [19]
Woodson

[11] Patent Number: 5,462,644
[45] Date of Patent: Oct. 31, 1995

[54] BIOFILM REDUCTION METHOD

[75] Inventor: Lewis P. Woodson, Apple Valley, Minn.

[73] Assignee: Minnesota Mining and Manufacturing Company, Saint Paul, Minn.

[21] Appl. No.: 257,877

[22] Filed: Jun. 10, 1994

Related U.S. Application Data

[62] Division of Ser. No. 816,157, Dec. 31, 1991.

[51] Int. Cl.$^6$ .................................. C02F 1/48; C02F 1/68
[52] U.S. Cl. ........................ 204/131; 210/748; 210/764
[58] Field of Search ........................... 204/131; 210/748, 210/764

[56] References Cited

U.S. PATENT DOCUMENTS

| | | | |
|---|---|---|---|
| 1,738,801 | 12/1929 | Shemitz | 204/403 |
| 1,902,390 | 3/1933 | Wormley | 204/141.5 |
| 3,774,246 | 11/1973 | Beer | 4/228 |
| 4,411,648 | 10/1983 | Davis et al. | 604/21 |
| 4,790,923 | 12/1988 | Stillman | 204/268 |
| 5,118,401 | 6/1992 | Oksman et al. | 204/228 |
| 5,129,999 | 7/1992 | Holland et al. | 204/131 |
| 5,302,345 | 4/1994 | Oksman et al. | 204/149 X |
| 5,312,813 | 5/1994 | Costerton et al. | 514/29 |

OTHER PUBLICATIONS

Khoury, A., et al., Patent Application, "Biofilm Reduction Method," May 3, 1991.

Rosenberg, B., et al., "Inhibition of Cell Division in *Escherichia coli* by Electrolysis Products from a Platinum Electrode," *Nature*, Feb. 13, 1965, vol. 205, pp. 698–699.

Sale, A., et al., "Effects of High Electric Fields on Microorganisms, I. Killing of Bacteria and Yeasts," *Biochim. Biophys. Acta*, 148 (1967) pp. 781–788.

Hamilton, W., et al., "Effects of High Electric Fields on Microorganisms, II. Mechanism of Action of the Lethal Effect," *Biochim. Biophys. Acta*. 148 (1967) pp. 789–800.

Pareilleux, A., et al., "Lethal Effects of Electric Current on *Escherichia coli*," *Applied Microbiology*, vol. 19, No. 3, pp. 421–424, Mar. 1970.

Rowley, B., "Electrical Current Effects on *E. coli* Growth Rates (36269)", Space Sciences Research Center, University of Missouri, Columbia, Mo., *Proceedings of the Society for Experimental Biology and Medicine*, vol. 139, No. 3, Mar. 1972, pp. 929–934.

Shimada, K., et al., "Responsibility of Hydrogen Peroxide for the Lethality of Resting *Escherichia coli* B Cells Exposed to Alternating Current in Phosphate Buffer Solution," *Agric. Biol. Chem.*, 46 46 (5), pp. 1329–1337, 1982.

Shimada, K., et al., "Leakage of Cellular Contents and Morphological Changes in Resting *Escherichia coli* B Cells Exposed to an Alternating Current," *Agric. Biol. Chem.*, 49 (12), pp. 3605–3607 (1985).

Davis, C., et al., "Ionotophoretic Killing of *Escherichia coli* in Static Fluid and in a Model Catheter System," *Journal of Clinical Microbiology*, vol. 15, No. 5, pp. 891–894 (May 1982).

Rootman, D., et al., "Iontophoresis of Tobramycin for the Treatment of Experimental Pseudomonas Keratitis in the Rabbit," *Arch. Ophthalmol.*, vol. 106, pp. 262–265 (Feb. 1988).

(List continued on next page.)

*Primary Examiner*—Donald R. Valentine
*Attorney, Agent, or Firm*—Gary L. Griswold; Walter N. Kirn; Jennie G. Boeder

[57] ABSTRACT

A method of killing microorganisms which form a biofilm on surfaces, including the surfaces of medical articles or on tissue or implant surfaces in a living subject. Killing of biofilm microorganisms is accomplished by applying an electric field to an electrically conductive medium in which the biofilm is contained. The electrically conductive medium either includes a biocide or is capable of generating a biocide in situ upon application of an electric field. A means of utilizing the method in vivo and a sterilizer are disclosed.

23 Claims, 2 Drawing Sheets

OTHER PUBLICATIONS

Hobden, J., et al., "Ionotophoretic Application of Tobramycin to Uninfected and *Pseudomonas aeruginosa*-Infected Rabbit Corneas," *Antimicrobial Agents and Chemotherapy*, vol. 32, No. 7, pp. 978–981 (Jul. 1988).

Davis, C., et al., "Effects of Microamperage, Medium, and Bacterial Concentration on Iontophoretic Killing of bacteria in Fluid," *Antimicrobial Agents and Chemotherapy*, vol. 33, No. 4, pp. 442–447 (Apr. 1989).

Eisenberg, E., et al., "Quantitative Association Between Electrical Potential Across the Cytoplasmic Membrane and early Gentamicin Uptake and Killing in *Staphylococcus aureus*", *Journal of Bacteriology*, vol. 157, No. 3, pp. 863–867 (Mar. 1984).

Shimada, K., et al., "Effect of alternationg current exposure on the resistivity of resting *Escherichia coli* B cells to crystal violet and other basic dyes," *Journal of Applied Bacteriology*, No. 62, pp. 261–268 (1987).

Rowley, B., et al. "The Influence of Electricl Current on an Infecting Microorganism in Wounds," *Annals New York Academy of Sciences*, vol. 238, pp. 543–550 (1974).

Ebert, L. Ya., et al., "Changes in Bacteria Sensitiviy to Antibiotics Under the Action of Direct Electro Current and Products of Medium Electrolysis," *Antibiotik*, vol. 16, No. 7, pp. 641–643 (Jul. 1971). (English language translation enclosed.)

Pamphlet entitled "Bacteria–Free Water, Therapeutic Water, Electrolytically," Model 320, by Ster–o–lizer Manufacturing Corporation, Salt Lake City, Utah (Mar. 1984).

"Sporocidal Efficiency of Two Ster–o–lizer Units," Lab. No. 10836, Nelson Laboratories, Inc., University of Utah Research Park, Salt Lake City, Utah, Report Date: 17 Jun. 1986).

"Ster–o–lizer MD–200 Efficacy Test," Microbiological test #62356 performed by UBTL, Inc., University of Utah Research Park, Salt Lake City, Utah (Start Date: 17 Jun., 1986; Completion date: 01 Jul. 1986).

Product literature entitled "Bacteria–Free Water" Halogent Generator Model 3800, by Ster–o–lizer Manufacturing Corporation, Salt Lake City, Utah (Jul. 1982) and attached letter dated Jan. 13, 1984 to Mr. Themy from Ms. Pendergrass.

Product literature entitled "Bacteria–Free Water" Ster–o–lizer Model 320, by Ster–o–lizer Manufacturing Corporation, Salt Lake City, Utah (Jul. 1982).

Product literature entitled "Bacteria–Free Water" Ster–o–lizer Model 100, by Ster–o–lizer Manufacturing Corporation, Salt Lake City, Utah (not dated).

Product literature entitled "Bacteria–Free Water" Ster–o–lizer Models 302 and 304, by Ster–o–lizer Manufacturing Corporation, Salt Lake City, Utah (Jul. 1982).

Laboratory Number 29228, Halogenics, Water Sterilizer, Model 304, Microbiological Development & Control, Inc., University of Utah research Park, Salt Lake City, Utah (1980).

Product literature entitled "The Ultimate Sterilizer, 3 Minute Cold/Wet Sterilizer" (1986); and Endoscope Sterilizer, for Models MD–200 and MD–201 (1987) and attached letter dated Nov. 28, 1986 to Tim Themy from J. R. Nelson.

Product literature entitled "Electrolytic Chlorozone Generator, Ster–o–lizer Model 210 Water Sterilizer", by Halogenic Products Corp., Salt Lake City, Utah (not dated).

Product literature entitled "Bacteria Free Whey," Halogen Generator 3700, Ster–o–lizer Manufacturing Corporatin, Salt Lake City, Utah (Jul. 1982).

Product literature entitled "Bacteria–Free Water and Charcoal Filtered Water," Ster–o–lizer Model 501, by Ster–o–lizer Manufacturing Corporation, Salt Lake City, Utah (Nov. 1982).

Product literature entitled "The 'Gold Generator'," by Ster–o–lizer Manufacturing Corporation, Salt Lake City, Utah (Jul. 1985).

Product literature entitled "The Bleacher" by Ster–o–lizer Manufacturing Company, Salt Lake City, Utah (Jul. 1985).

Product literature entitled "The Pulper" by Ster–o–lizer Manufacturing Company, Salt Lake City, Utah (Dec. 1984).

Product literature entitled "Cyanide–Free Water" Nutr–o–lizer Model 301 and Voltage Controller Model VC–125, by Ster–o–lizer Manufacturing Company, Salt Lake City, Utah (Nov. 1982).

Product literature entitled "Bacteria–Free Pathogen–Free Sterile Sea Water Without Filters, Chemicals, Ultra Violet Lights, Boiling, Reverse Osmosis, Etc.!," Halogen Generator Model 3500, by Ster–o–lizer Manufacturing Company, Salt Lake City, JT (Jul. 1981).

Product literature entitled "Amazing Technological Breakthrough! For Coolant Users," Ster–o–lizer Model 300, by Ster–o–lizer Manufacturing Company, Salt Lake City, Utah (no date).

Product literature entitled "Automatically! Algae–Free Chlorine–Free Chemical–Free Sterile Pool Water," by Halogenic Products Corporation, Salt Lake City, Utah; and letter dated Dec. 30, 1965 To: All Local Health Officers.

Product literature entitled "Brinecell Electrochemical Generator of Germicidal Agents" (Model 336), by Ster–o–lizer Manufacturing Company, Salt Lake City, Utah (Feb. 1985).

Product literature entitled "60–Second Cold Sterilizer for All Types of Scientific and Surgical Instruments, Disposable and Nondisposable, Without Gas, Heat, UV, Radiation or Chemicals," Model MD–200, Ster–o–lizer Manufacturing Corporation, Salt Lake City, JT (Revised from Oct. 1985) and Retail Price effective Oct. 1985).

Product literature entitled "Disposable and Nondisposable Surgical Instrument Sterilizer," Ster–o–lizer Model MD–200, Ster–o–lizer Manufacturing Corporation, Salt Lake City, Utah, Revised Form No. 6 (Nov. 1982) and attached study from the 59th Convention of the Japanese Society of Medical Device General Subjects.

Costerton, J., et al., "Bacterial Biofilms in Nature and Disease," *Annual Review of Microbiology*, Annual Reviews, Inc., Palo Alto, Calif., vol. 41, pp. 435–464.

Costerton, J., et al., "The Bacterial Glycocalyx in Nature and Disease," *Ann. Rev. Microbiol.*, vol. 35, pp. 299∝324 (1981).

Gristina, A., et al., "Bacterial Adherence and the Glycocalyx and Their Role in Musculoskeletal Infection," *Orthopedic Clinics of North America*, vol. 15, No. 3, pp. 517–535 (Jul. 1984).

LeChevallier, M., et al., "Inactivation of Biofilm Bacteria," *Applied and Environ. Microbiol.*, vol. 54, No. 10, pp. 2492–2499 (Oct. 1988).

Jacques, M., et al., "Review: Microbial Colonization of Prosthetic Devices," *Microb. Ecol.*, No. 13, pp .173–191 (1987).

Nickel, J., et al., "Tobramycin Resistance of *Pseudomonas aeruginosa* Cells Growing as a Biofilm on Urinary Catheter Material", *Antimicrobial Agents and Chemotherapy*, vol. 27, No. 4, pp. 619–624 (Apr. 1985).

Nickel, J., et al., "Antibiotic Resistance of *Pseudomonal aeruginosa* Colonizing a Urinary Catheter in Vitro," *Eur. J.*

*Clin. Microbiol.*, vol. 4, No. 2, pp. 213–218 (Apr. 1985).

Passerini, L., et al., "Biofilms on Right Heart Flow–directed Catheters," *Chest*, vol. 92, No. 3, pp. 440–446 (Sep. 1987).

Pedersen, P., et al., "Ion motive ATPases. I. Ubiquity, properties and significance to cell function," *Trends in Biochemical Sciences*, Elsevier Publ., Cambridge, Ref. vol. 12, pp. 146–150 (1987).

Read, R., et al., "Peritonitis in peritoneal dialysis: Bacterial colonization by biofilm spread along the catheter surface," *Kidney International*, vol. 35, pp. 614–621 (1989).

Reed, W., et al., "Bacterial colonization of Hemasite access devices," *Surgery*, vol. 99, No. 3, pp. 308–317 (Mar. 1986).

Warren, J., et al., "A Prospective Microbiologic Study of Bacteriuria in Patients with Chronic Indwelling Urethral Catheters," *The Journal of Infectious Diseases*, vol. 146, No. 6, pp. 719–723 (Dec. 1982).

BIOFILM REDUCTION METHOD

This is a division of application Ser. No. 07/816,157 filed Dec. 31, 1991.

FIELD OF THE INVENTION

The present invention relates to a method of biofilm reduction and to devices designed to facilitate biofilm reduction.

REFERENCES

Nature, 205:698–699 (1965).

Sale, A. J. H. and Hamilton, W. A., Biochim. Biophys. Acta., 148:781–788 (1967).

Hamilton, W. A. and Sale, A. J. H., Biochim. Biophys. Acta., 148:789–800 (1967).

Pareilleux, A. and Sicard, N., Applied Microbiology, 19(3):421–424 (1970).

Rowley, B.A., P.S.E.B.M., 139:929–934 (1972).

Shimada, K. and Shimahara, K., Agric. Biol. Chem., 46(5):1329–1337 (1982).

Shimada, K. and Shimahara, K., Agric. Biol. Chem., 49(12):3605–3607 (1985).

Ebert, L.Ya. and Evtushenko, A. D., Antibiotik, 16[7]:641–643 (1971).

Rowley, B. A., McKenna, J. M. and Chase, G. R., Annals New York Academy of Sciences, 238:543–551 (1974).

U.S. Pat. No. 4,411,648 (Davis et al.).

Davis, C. P., Arnett, D. and Warren, M. M., Journal of Clinical Microbiology, 15(5):891–894 (1982).

Rootman, D. S. et al., Arch Ophthalmol, 106:262–265 (1988).

Hobden, J. A. et al., Antimicrobial Agents and Chemotherapy, 32(7):978–981 (1988).

Davis, C. P. et al., Antimicrobial Agents and Chemotherapy, 33(4):442–447 (1989).

Costerton, J. W., et al., Ann. Rev. Microbiol. 41:435–464 (1987).

Costerton, J. W., Irvin, R. T., Cheng, K.-J., Ann. Rev. Microbiol. 35:299–324 (1981).

Gristina, A. G. and Costerton, J. W., Ortho. Clin. of N. America 15:517–535 (1984).

Jacques, M., Marrie, T. J., Costerton, J. W., Microb. Ecol. 13:173–191 (1987).

LeChevallier, M. W. et al., Appl. Environ. Microbiol. 54:2492–2499 (1988).

Nickel, J. C., et al., Antimicrob. Agents Chemother. 27:619–624 (1985).

Nickel, J. C., Wright, J. B., Ruseska, I., Marrie, T. J., Whitfield, C., and Costerton, J. W., Eur. J. Clin. Microbiol. 4:213:218 (1985).

Passerini, L., Phang, P. T., Jackson, F. L., Lam, K., Costerton, J. W., King, E. G., Chest 92:440–446(1987).

Pederson, P. L. et al., Trends Biochem Sci, 12:146 (1987).

Read, R. R., Eberwein, P., Dasgupta, M. K., Grant, S. K., Lam, K., Nickel, J. C., and Costerton, J. W., Kidney Int'l 35:614–621 (1989).

Reed, W. P., Moody, M. R., Newman, K. A., Light, P. D., Costerton, J. W., Surgery 99:308–317 (1986).

Warren, J. W., Tenney, J. H., Hoopes, J. M., Muncie, H. L., Anthony, W. C., J. Inf. Duo 146:719–723 (1982).

BACKGROUND OF THE INVENTION

A number of references describe the effects of electric current upon planktonic microorganisms (Nature, Sale, Hamilton, Pareilleux, Rowley (1972), Shimada (1982), Shimada (1985), Ebert). Various causes for the lethal effects of electric current are proposed. Rowley (1974) describes the effects of direct current in reducing the viability of infecting microorganisms using a rabbit model. The application of direct current to a surface wound was shown to enhance antibiotic activity.

Iontophoretic devices are also well known (U.S. Pat. No. 4,411,648, Davis (1982), Rootman, Hobden, Davis (1989)). Iontophoresis is a process whereby an agent can be driven into surrounding tissue or a fluid path by application of an electric current.

None of the previously described references describe methods or devices which utilize electric current to kill or reduce biofilms. A biofilm is a conglomerate of microbial organisms embedded in a highly hydrated matrix of exopolymers, typically polysaccharides, and other macromolecules (Costerton 1981). Biofilms may contain either single or multiple microbial species and readily adhere to such diverse surfaces as river rocks, soil, pipelines, teeth, mucous membranes, and medical implants (Costerton, 1987). By some estimates biofilm-associated cells outnumber planktonic cells of the same species by a ratio of 1000–10,000:1 in some environments.

Prevention of colonization by and eradication of biofilm-associated microorganisms is an important, and often difficult to solve, problem in medicine. Unlike planktonic organisms, which are relatively susceptible to biocides, e.g., antibiotics, the structural matrix established during biofilm formation can make the colonizing cells able to withstand normal treatment doses of a biocide. It is known that when organisms are isolated from biofilms and then grown in planktonic culture, they lose many of the characteristics associated with the progenitor cells, in particular, the ability to produce a glycocalyx (Costerton, 1987). In the biofilm, the glycocalyx matrix appears to serve as a barrier which protects and isolates the microorganisms from host defense mechanisms, such as antibodies and phagocytes, as well as from antimicrobial agents including surfactants, biocides and antibiotics (Costerton, 1981). In one study, biofilm-associated bacteria were able to survive a concentration of antibiotic 20 times the concentration effective to eliminate the same species of bacteria grown in planktonic culture (Nickel, 1985).

Biofilm infections can occur in a variety of disease conditions. In some tissue infections, such as prostatitis, the infective bacterium is capable of growing in the infected tissue in both biofilm (sessile) and circulating (planktonic) form (Costerton, 1987). Although growth of the planktonic cells can be controlled by antibiotic treatment, the biofilm itself may be refractory to treatment, providing, in effect, a reservoir of infection which can lead to recurrence of the infection after antibiotic treatment.

Biofilm formation can also be a serious complication in bioimplants, such as bone prosthesis, heart valves, pacemakers and the like. Biofilm formation on exposed surfaces of a bioimplant can degrade the function of the implant (Passerini), as in the case of implanted valves, lead to serious joint or bone infections, as in the case of a bone prosthesis (Gristina), and in all cases, provide a source of difficult-totreat septic infection (Jacques).

SUMMARY OF THE INVENTION

The present invention provides a method of killing microorganisms in a biofilm comprising suspending the biofilm or biofilm infected device in an electrically conductive medium and applying an electric field to the solution, the source of electric field being remote from the biofilm and the electric field strength and duration of application being sufficient to produce killing of the microorganisms in the biofilm. The biofilm is not in direct contact with the electrodes or source of the electric current. Preferably, the electric field strength and duration of application are sufficient to reduce biofilm microorganisms by at least 3 logs.

The invention also provides a method of enhancing the action of biocides in killing biofilms comprising administering to the biofilm a biocide in an amount which would be ineffective to kill microorganisms in the biofilm if used alone, and exposing the biofilm in an electrically conductive medium to an electric field as described above.

The invention further provides a method and device for disinfecting or sterilizing devices infected with biofilms. The biofilm infected device is placed in an electrolyte solution and an electric field is applied across the solution. The device is effective to kill microorganisms in the biofilm and disinfect or sterilize the device whether or not biocides are added to electrolyte solution. When biocides are included they are preferably present in a concentration which is less than effective to kill the biofilm microorganisms in the absence of the electric field. The electric field is preferably generated by currents between the electrodes of at least 1 to 200 milliamps, most preferably between 1 and 50 milliamps.

Biofilms frequently form on a surface expanse, such as medical instruments, urinary catheters, prosthetic devices, i.e., artificial hips and knees, and contact and intraocular lenses. The biofilm is refractory to killing when a biocide is contacted with the biofilm at a planktonic biocidal concentration (PBC), i.e., that concentration which is effective in killing the microorganism in a planktonic, but not in a biofilm form. However, when the biofilm is placed in an electrically conductive medium with the biocide at a concentration which alone would be ineffective to kill the biofilm, and an electric field is applied through the solution, the strength and duration of the current are such as to produce killing of microorganisms forming the biofilm.

In a typical embodiment, the biofilm is composed predominantly of bacteria, yeast, fungi or mold. The biocide can be an antibiotic, such as one of the penicillins, cephalosporins, aminoglycosides, tetracyclines, sulfonamides, and quinolones, or may be a disinfectant or sterilant. Alternatively the biocide may be generated in situ upon application of an electric field to the electrically conductive medium.

The electric field is preferably applied across a pair of electrodes in an electrically conductive solution, at a voltage level sufficient to produce a current between the electrodes of at least about 1 to 200 milliamp.

For treating infected regions in vivo, the electric field may be applied across the effected region by a non-invasive electrical field generating device.

The features of the invention will become more fully apparent when the following detailed description of the invention is read in conjunction with the accompanying drawings.

DETAILED DESCRIPTION OF THE INVENTION

A. Biofilm Formation and Characteristics

Figure 1:
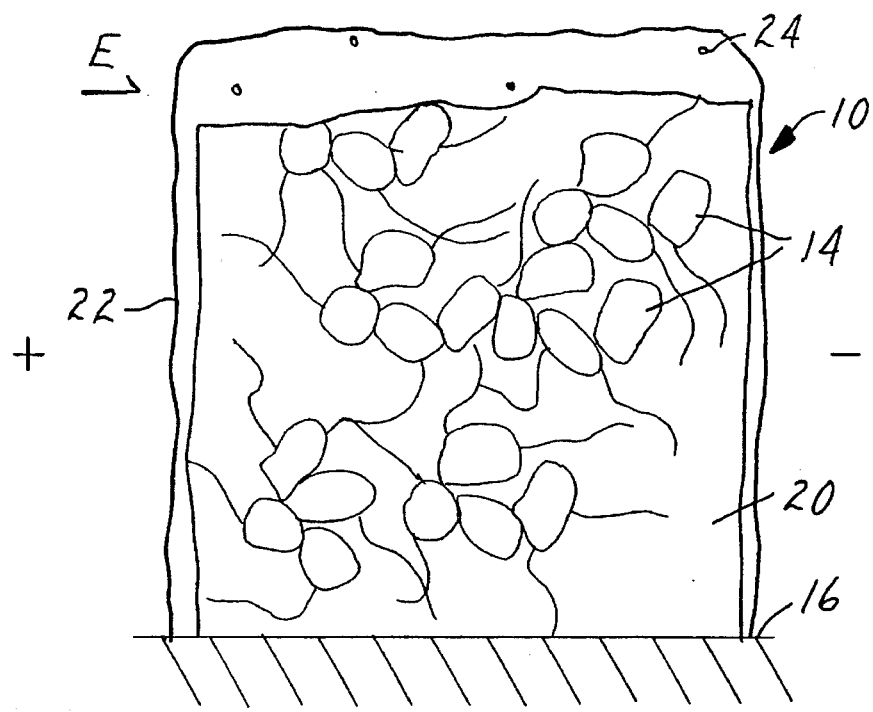
FIG. 1 illustrates a surface expanse and a biofilm growing on the expanse.

Biofilms are composed of colonies of microorganisms, typically bacterial cells, but also colonies of yeast, fungi, mold or other colonizing microorganisms. FIG. 1 is a representation of a biofilm 10 formed of clumps or colonies of cells, such as cells 14, which are anchored to a surface expanse 16.

The cells in a biofilm are embedded in a hydrated matrix of exopolymers and other filamentous macromolecules, typically glycopeptides, such as indicated at 20 in FIG. 1. The matrix formed by the filamentous material serves to anchor and coalesce the cells in the biofilm. The matrix, along with other cellular changes which occur on colonization, serves to protect colonized cells against biocidal agents to which the biofilm may be exposed, as discussed below.

The surface expanse and biofilm formed thereon are in contact with an aqueous medium, indicated at 22. The medium may be a defined electrolyte solution or a body fluid, such as blood or lymph, which supplies the tissue on which the biofilm is formed. The medium may carry planktonic cells onto the biofilm, where the cells may become incorporated in the biofilm; conversely, sessile cells in the biofilm may break off, individually or in clumps to form part of the circulating cell population.

In accordance with the present invention, the aqueous medium in contact with the biofilm contains a biocide (either an added biocide or one generated in situ by an electric field), such as indicated by biocide molecules 24. As noted above, the microorganisms in the biofilm have a substantially higher tolerance for the biocide than the same microorganisms in free, i.e., planktonic form.

The greater resistance to biocides of microorganisms in a biofilm, when compared with the same cells in planktonic form, has been established for a variety of microorganisms. Among bacteria, this phenomenon has been shown for *P. Aeroginosa, Klebsiella pneumoniae, E. coli* and *Staphylococcus epidermidis*. The concentration of antibiotic needed to kill substantially all cells in biofilm, herein referred to as the biofilm biocidal concentration (BBC), can range from 2 up to 50 times the concentration required for substantially complete killing in planktonic form, also known as the planktonic biocidal concentration (PBC). Similarly, it has been shown that yeast-cell biofilms are resistant to much higher concentrations of antibiotic, such as cycloheximide, than the yeast cells in planktonic form.

Figure 2:
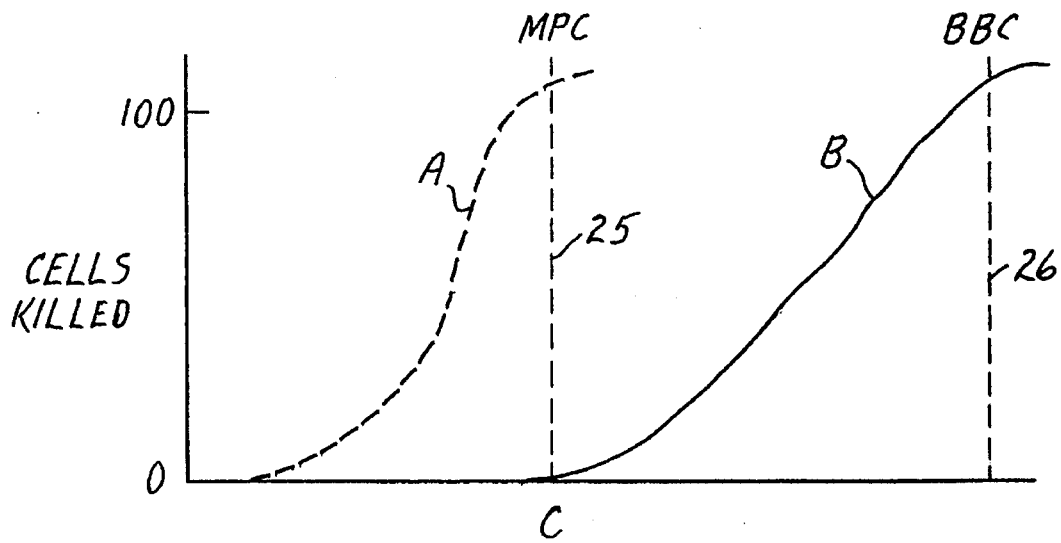
FIG. 2 is a hypothetical concentration-effect curve for biocidal killing of planktonic (dotted line A) and biofilm (solid line B) microorganisms.

FIG. 2 shows an idealized dose-response curve for bacterial cell killing at increasing concentration of antibiotic, for cells in planktonic (dotted line A) and biofilm (solid line B) form. The line indicated at 25 in the figure is the PBC concentration at which substantially all of the planktonic cells are killed. As seen, only a relatively small percent of biofilm cells are killed at this concentration.

Although more of the biofilm cells will be killed at biocide concentrations above the PBC, increasingly higher drug levels may be impractical or undesirable, particularly at concentrations needed to kill substantially all of the biofilm cells. As will be seen below, and according to an important feature of the present invention, it has been discovered that the biofilm dose-response curve for cell viability can be shifted toward lower drug concentration by subjecting the biofilm cells to an applied electric field. Typically, this shift has the effect of producing substantially complete biofilm cell killing at concentrations at or below the PBC, and below the biofilm biocidal concentration (BBC) needed to produce complete biofilm killing under normal (zero electric field) conditions, indicated by line 26 in FIG. 2.

With reference again to FIG. 1, the biofilm 10 is shown in an electric field E generated by placing a voltage potential across a pair of electrodes, indicated by "+" and "−" electric polarity symbols. Ions in the biofilm and surrounding electrolyte medium serve as current carriers between the two electrodes.

According to an important feature of the invention, it has been discovered that a biofilm is substantially more susceptible to cell killing by a biocide (either an added biocide or one generated in situ by an electric field) when the biofilm is placed in an electrolyte medium through which an electric field is applied. As will be seen, the electric field is effective to produce killing of biofilm cells at biocide concentrations which are several times lower than normal biofilm biocide concentrations. That is, the electric field shifts the biofilm biocide curve in FIG. 2 toward substantially lower concentrations.

B: Biofilm Reduction by. Application of an Electric Field

Figure 3:
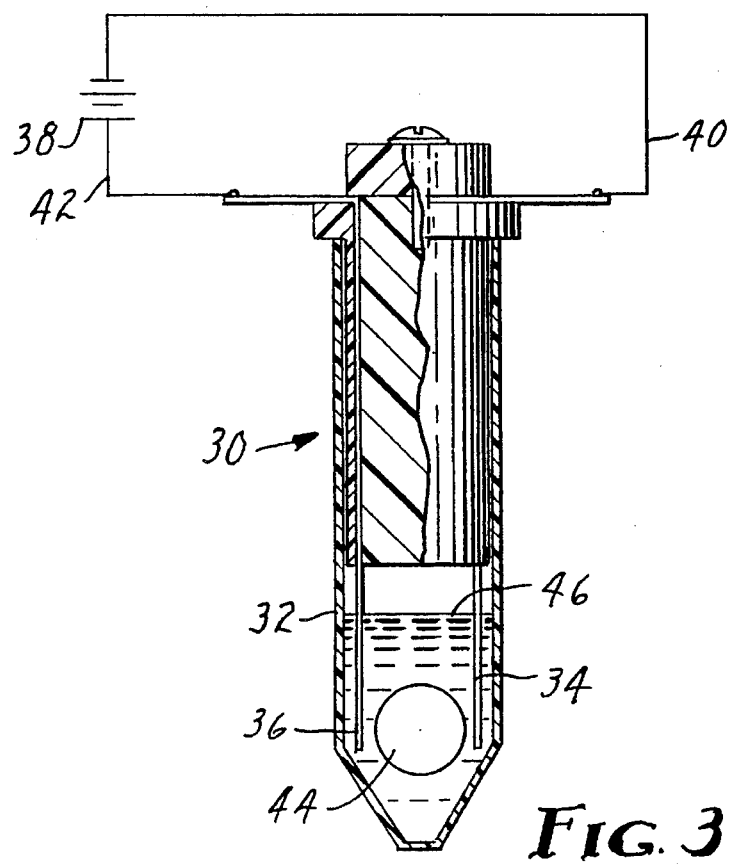
FIG. 3 shows an experimental device used for testing the effect of an electric field on the viability of biofilm cells.

FIG. 3 shows a system for demonstrating the effects of an electric field on biofilm cells, with or without the use of a biocide. The system or biofilm test device 30 includes a housing 32 formed from a conical polystyrene tube fitted with a pair of platinum electrodes, 34 and 36, which extend into the lower portion of housing 32, as shown, and which are connected to the opposite sides of a voltage source 38, using stainless steel wires, 40 and 42, respectively.

In operation a biofilm coated polymethylmethacrylate disk 44 (22 mm diameter and 4 mm thick), prepared as described in the Examples, is placed within tube 32 into a suitable electrolyte solution 46. Typically, the biofilm formed on disk 44 has a colony forming concentration of between about $10^6$ and $10^7$. The electrolyte solution is one which is comprised of strong electrolytes such as sodium and calcium, and is capable of conducting a current between 1 and 200 milliamps. Electrolyte solutions which are useful have conductivities of between 2.2 and $8 \times 10^5$ ohms/cm. The electrolyte solution may contain an added biocide at a selected concentration.

Thereafter, a current is applied across device 30, exposing biofilm coated disk 44 to an electric field. After a selected treatment time, the disk 44 is removed aseptically and analyzed for viable cells.

Using the device 30 depicted in FIG. 3, biofilm cell viability was determined after treatment with various biocides, with and without application of electric field, and with application of electric field alone. In some cases, any electrically generated biocides were neutralized by addition of an agent specific for the electrically generated biocide, to the electrolyte solution.

As reported in Example 1, electric field alone is effective in eradicating both planktonic and biofilm bacteria. When planktonic and biofilm bacteria (*Escherichia coli* and *Staphylococcus epidermidis*) were exposed in an electrolyte solution of phosphate buffered saline, which contained no additional biocide, the planktonic bacteria were completely eradicated after exposure to 10 milliamps for one hour, and the biofilm bacteria was completely eradicated after exposure to 30 milliamps for one hour. It is thought that this lethal effect is due to electrolytically generated in situ biocides, such as active chlorine, superoxides, free radicals and heavy metal ions (Shimada (1982), Pareilleux, Hamilton). Example 2 confirms this theory by illustrating that neutralization of the in situ generated biocides renders the electric field ineffective to eradicate even planktonic bacteria.

However, when the electrolytically generated biocides are neutralized, we have demonstrated that electric field enhances the effects of added biocides and enables them to be effective in killing both planktonic and biofilm bacteria at concentrations much lower than is effective in the absence of an electric field. As shown in Examples 3 and 4, treatment with electric field alone (10, 15 and 20 milliamps), or with biocide alone (0.25 to 250 ug/ml of Kanamycin A Monosulfate (Example 4) or 25 to 25,000 units/ml of Penicillin G (Example 3)) has no appreciable effect on log reduction of the biofilm microorganisms after eight hours. By contrast, exposing the biofilms to electric fields in the presence of added biocides, of the same strengths and concentrations for the same time periods, results in significant log reduction of the biofilm microorganisms. The results reported in Tables 3 and 4 indicate that the effect of electric field and biocide upon biofilm microorganism viability is synergistic.

Examples 5, 6, and 7 illustrate the enhanced effect that can be achieved by utilizing an electric field in combination with a glutaraldehyde sterilant solution ("Glutarex™ Disinfecting and Sterilizing Solution", commercially available from 3M, St. Paul, Minn.). Treatment in 2% by volume glutaraldehyde caused a reduction in both planktonic and biofilm bacterial (Bacillus subtilis) over time. However, the combination of treatment with 2% glutaraldehyde and application of an electric field to the sterilant solution caused complete sterilization within a much shorter period of time than was achieved with glutaraldehyde alone.

The studies described above are illustrative of the general method of the invention, demonstrating the effectiveness of electric field, in combination with biocides which are added or electrolytically generated, in reducing biofilm cell viability. Biocide concentrations which themselves are relatively ineffective in killing biofilm microorganisms are usefully employed to kill biofilm bacteria when used in combination with an electric field. Bacterial, yeast, fungus and mold cell biofilms can be treated effectively. Electrolytically generated in situ biocides, as well as a variety of added biocide compounds, including compounds from different families of antibiotics, antifungal agents, sterilants and disinfectants are useful in the treatment method.

Where a biocide additive is used in the method, it is one which is selected, according to known pharmaceutical principles, for effective killing of the infecting microorganism. For example, an appropriate biocide may be selected by testing a culture of the bacterial cells against a panel of biocides. Among the biocides which are useful in the present invention are active chlorines such as, sodium hypochlorite, calcium hypochlorite, elemental chlorines, hypochlorous acid, hypochlorite ion, and chlorine dioxides; quaternary ammonium compounds such as monoalkyltrimethyl ammonium salts, monoalkyldimethylbenzyl ammonium salt, dialkyldimethyl ammonium salts, heteroaromatic ammonium salts, polysubstituted quaternary ammonium salts, bis quaternary ammonium salts, and polymeric quaternary ammonium salts; heavy metals such as silver, cobalt, copper, iron, lead, gold, silver, mercury, nickel, zinc, aluminum, stannous, tin, manganese, and platinum; peroxides such as hydrogen peroxide, peroxyacetic acid, peroxyhaptanoic acid, peroxynonanoic acid, monoperglutaric acid, succinyl peroxides, and diperglutaric acid; and aldehydes such as glutaraldehyde, formaldehyde, glyoxal, malonaldehyde, succinaldehyde, and adipaldehyde. Among the antibiotics which are useful in the present invention are those in the penicillin, cephalosporin, aminoglycoside, tetracycline, sulfonamide, macrolide antibiotics, and quinoline antibiotic families. Preferred antibiotics also include imipenem, aztreonam, chloramphenicol, erythromycin, clindamycin, spectinomycin, vancomycin, and bacitracin. Among the preferred anti-fungal agents are the imidazole compounds, such as ketoconazole, and the polyene microlide antibiotic compounds, such as amphotericin B.

The desired biocide concentration, whether added or electrolytically generated, is one which is ineffective in killing biofilm microorganisms when applied in the absence of an electric field. Where the method of the invention is used to killing biofilms in vitro, by passing an electric field through an electrolyte medium containing a biofilm contaminated device, as illustrated in the configuration in FIG. 3, the biocide may be added at an appropriate concentration below the BBC to an aqueous medium containing electrolyte(s) which serve as current carriers. Typically, concentrations of biocide between 1 ng/ml and 1 g/ml, preferably 1 ug/ml to 1 mg/ml, are employed.

Where the method is used in the treatment of a biofilm in vivo, the biocide may be administered at doses, and dosing intervals sufficient to produce effective concentrations of the biocide in the region of the biofilm. Typically, an antibiotic is administered at regular intervals over a 3–7 day period to achieve substantially complete bacterial cell killing. The biocide which is administered typically reaches the biofilm site via the bloodstream or lymphatic system, and thus contacts the biofilm via the body fluid. The body fluid provides a conductive medium for the biofilm, in addition to providing a carrier system for the biocide. After the biocide is administered, and reaches a threshold level at the biofilm site, the effect of the biocide in biofilm killing is enhanced by applying an electric field across that portion of the body containing the biofilm.

The electric field is applied by a voltage source, which may supply a direct current (DC) source, such as a battery, or a conventional alternating current (AC) or pulsed voltage source. The voltage level is typically set to between 0.5–20 volts, preferably between 1–10 volts, and preferably under conditions effective to generate a current of at least about 1–50 milliamp or greater between the electrodes which form the electric field. The effectiveness of the electric field on biofilm destruction will depend on the strength of the electric field, which in turn depends on the voltage and distance between electrodes, the duration of field application, the concentration of biocide at the biofilm during application of the electric field, and fluctuations in the field. The electric field is applied until a desired reduction in biofilm is achieved, as determined for example by testing cell viability on a biofilm surface. For in vivo treatment of biofilm infection, the treatment method may be monitored, for example, by assaying for infecting microorganisms systemically or near the site of biofilm infection.

C. Applications

In one general embodiment, the method of the invention is used for reducing biofilms in vitro, by placing a biofilm infected device into an electrolyte medium, optimally containing an added biocide, and applying an electric field. This application is demonstrated generally by the systems shown in FIGS. 3 and 4, where a biofilm infected device is placed in an electrolyte medium between two electrodes. As demonstrated in this system, the electric field enhances the biocidal effect of the in situ generated biocides or any added biocides, as judged by the loss of biofilm cell viability at biocide concentrations which are normally ineffective in killing biofilm cells.

In a second general embodiment, the method is used for treating biofilm infection in the body, by applying an electric field across that portion of the body containing the biofilm. The method of the invention is applicable to disease conditions which involve biofilm growth on a natural tissue surface or bio-implant surface. Included are procedures involving catheters, vascular access parts, shunts, and other temporary indwelling devices, as well as permanent prosthetic devices such as artificial valves, knees, hips, which have the potential to become contaminated with a biofilm.

For example, in peritoneal dialysis by an in-dwelling catheter, where biofilm formation is known to be a source of continued infection (Read), the biofilm may be treated by administering an antibiotic for delivery into the peritoneal cavity, and generating an electric field through the peritoneal cavity using a noninvasive electric field generating device for example, the field could be generated by electrode pads placed on either side of the patient in the region of the peritoneal cavity.

The biocide used in the treatment method is preferably an orally administered antibiotic which appears in the urine, at a PBC concentration or higher, within 1 to 4 hours after administration. Preferred antibiotics which are useful against gram-negative bacteria include broad-spectrum penicillins, such as ticarcillin, sulfonamides, and cephalosporins. These drugs may be used in combination with each other, with other antibiotics such as parenterally-administered aminoglycosides, or in combination with other drug-enhancing agents such as penicillinase inhibitors (clavulanate, sulbactam) or as in the combination of sulfamethoxazole with imethoprim.

After drug administration, a preferably 1–5 volt potential is applied, and the resulting electric field is applied for typically 1–4 hours during maximum concentration of antibiotic agent in the urine. The treatment may be repeated at periodic intervals, e.g., once a day during the period of catheter use, to insure that biofilm growth is suppressed during the period of catheter use.

Similarly, bacterial colonization of a Hemasite access device (Reed) can be controlled, particularly in the transcutaneous regions, by combining electric field generation with antibiotic administration, such as topically in the transcutaneous zones.

Prostate infection commonly occurs spontaneously or as a complication of chronic catheterization in elderly males. Under usual treatment methods, the patient is given an antibiotic treatment which may involve oral doses of ampicillin or one of the cephalosporins over a 7- to 10-day dosing period. This treatment is generally effective to eliminate symptoms of localized infection. However, infection may recur within a several-month period, evidencing latent infection, presumably in a biofilm reservoir, which was not destroyed by the antibiotic treatment.

In the present treatment method, antibiotic administration is accompanied by electric field generation through the prostate region. In the treatment method, an antibiotic, such as ticarcillin, cefaclor or gentamicin is administered orally, intramuscularly, or intravenously to the patient. When the antibiotic has reached a desired level in the region of infection, an electric field in the region of the prostate gland is applied by a noninvasive electric field generating device to produce the desired electric field in the region of the biofilm. The electric field is applied typically for 1–4 hours during maximum concentration of antibiotic agent in the infected region. The treatment may be repeated at periodic intervals, e.g., once a day over a two-week period, to insure that biofilm growth is eliminated.

Figure 4:
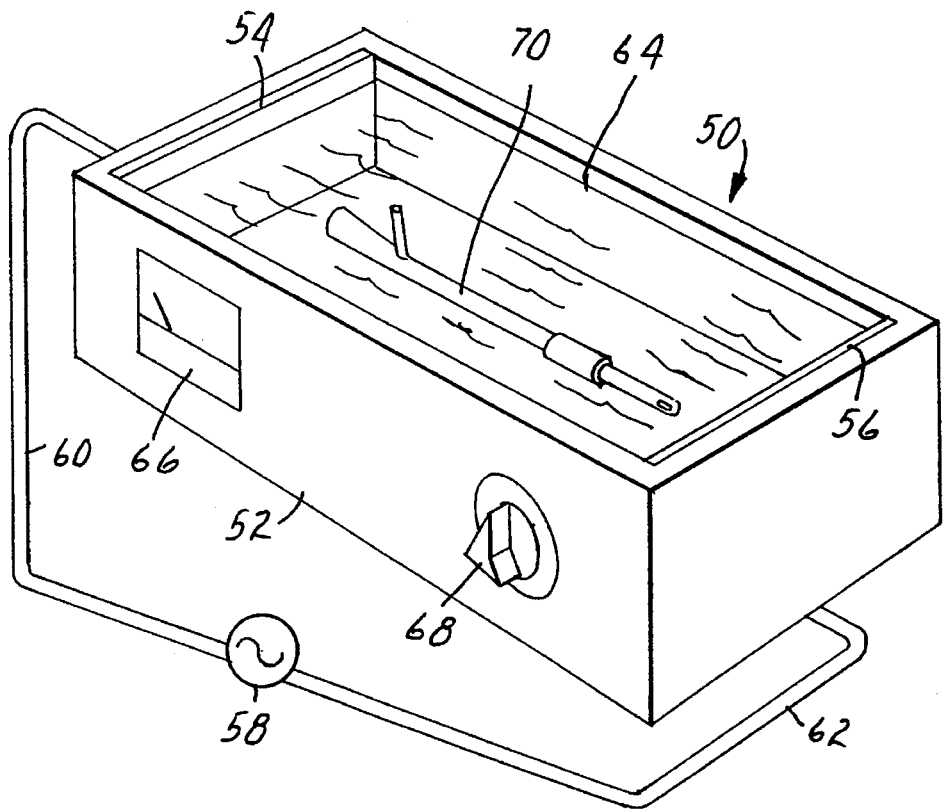
FIG. 4 illustrates a sterilizer, in accordance with an embodiment of the invention.

The increasing use of medical and surgical materials and devices that cannot be sterilized by normal steam or heat methods has resulted in an increased need for a safe, efficient cold-sterilization process. In another embodiment of the invention, a method is provided for sterilization of biofilm infected materials and devices by applying an electric field across an electrolyte solution which contains or is capable of electrolytically generating a biocide. FIG. 4 shows a sterilizer 50 which includes a housing 52 made of suitable nonconductive material, such as polycarbonate, polypropylene, or insulated stainless steel. The housing defines an internal chamber and may have any useful dimensions but, as shown, is 50 cm by 20 cm. Opposing internal surfaces are electrodes 54 and 56 made preferably of platinum. Electrodes 54 and 56 are connected to opposite sides of a voltage source 58 using copper wires 60 and 62, respectively.

An electrolyte solution 64 at least partially fills the internal cavity of the device. The electrolyte solution is comprised of strong electrolytes such as sodium and calcium, and is capable of conducting a current of between 1 and 200 milliamps. Preferred electrolyte solutions include well known buffer systems such as Clark and Lubs solutions, pH 1.0–2.2 (Bower and Bates, J. Res Natn. Bur. Stand. 55, 197 (1955)); glycine-HCl buffer solutions, pH 2.2–3.6 at 25° C. (Sorenson, BZ 21, 131 (1909); Gomori, Meth. Enzmol. 1, 141 (1955)); Clark and Lubs solutions, pH 22–4.0 (Bower and Bates, J. Res Natn. Bur. Stand. 55, 197 (1955)); citric acid-$Na_2HPO_4$ (McIlvaine) buffer solution, pH 2.6–7.6 (McIlvaine, JBC 49, 183 (1921)); citric acid-sodium citrate buffer solutions, pH 3.0–6.2; beta,beta-dimethylglutaric acid-NaOH buffer solutions, pH 3.2–7.6 (Stafford, Watson, and Rand, BBA 18, 318 (1955)); sodium acetate-acetic acid buffer solutions, pH 3.7–5.6; succinic acid-NaOH buffer solutions, pH 3.8–6.0 (Gomeri, Meth. Enzymol. 1, 141 (1955)); sodium cacodylate-HCL buffer solutions, pH 5.07.4 (Pumel, Bull. Soc. Chim. Biol. 30, 129 (1948)); $Na_2HPO_4$—$NaH_2PO_4$ buffer solutions, pH 5.8–8.0 (Gomeri and Sorensons, Meth. Enzmol. 1, 143 (1955)); Clark and Lubs solution, pH 8.0–10.2 (Bower and Bates, J. Res Natn. Bur. Stand. 55, 197 (1955)); borate buffer solutions, pH 8.1–9.0 (Bates and Bower, Analyt. Chem. 28, 1322 (1956)); and phosphate buffer solutions, pH 11.0–11.9 (Bates and Bower, Analyt. Chem. 28, 1322 (1956)). The electrolyte solution preferably contains disinfectants or sterilants, such as active chlorines, quaternary ammonium compounds, heavy metals, peroxides and aldehydes.

The voltage source 58 may supply direct or alternating current. The voltage level is typically set between 0.5–20 volts, preferably between 1–10 volts, and preferably under conditions effective to generate a current of at least about 1–50 milliamps between electrodes 54 and 56. Additional optional features of the sterilizer include an amp meter 66, capable of recording currents passing through the electrolyte solution 64, and a timer 68 which regulates the duration of the electric field.

In use, a device potentially contaminated with a biofilm, such as catheter 70 is submerged in the electrolyte solution 64 within the sterilizer. The electrolyte solution preferably contains a disinfectant such as glutaraldehyde, present in a concentration of 2% by volume. An electric current of typically 20 ma is applied across the electrolyte solution for about 1 hour. As reported in Examples 5, 6, and 7, the combination of treatment with 2% glutaraldehyde and application of an electric field to the sterilant solution causes complete sterilization of biofilm contaminated materials. The electric field enhances the effectiveness of the sterilant by several orders of magnitude, as judged by a significant log reduction over time. The sterilizer may have wide-spread applicability for cold sterilization of various medical devices. A commercial use could be as a contact lens sterilizer.

From the foregoing, it can be appreciated how various objects and features of the present invention are met. The treatment method allows biofilm infections, which are often difficult or impossible to treat by biocide treatment alone, to be effectively controlled or eliminated at tolerated biocide levels, by enhancing the biocide effect selectively in the region of biofilm growth.

The electric field used for enhancing biocide effect is itself safe and generally easy to generate, either by direct connection to a voltage source, or by magnetic induction. The method is applicable to a wide range of biofilm infections involving both natural tissue surfaces or bio-implant surfaces.

The following examples illustrate specific treatment methods which demonstrate the application of the method to various bacterial organisms. The examples are intended to illustrate, but not limit, the scope of the invention.

Examples

Microorganisms

The following bacterial strains were used: *Escherichia coli* ATCC#8739, *Escherichia coli* ATCC#15221, *Staphylococcus epidermidis* ATCC™12228, and *Staphylococcus epidermidis* ATCC#35984, all commercially available from American Type Culture Collection (ATCC), Rockville, Md. The planktonic bacteria were grown overnight in sterile trypticase soy broth (TSB) (commercially available from Difco Laboratories, Inc., Detroit, Mich.) at 34° C., and harvested by centrifugation at 2300 rpm for 15 minutes. The bacteria pellets were washed twice with a sterile 0.01M phosphate buffered saline solution (PBS) (commercially available from Gibco Laboratories, Life Technologies, Inc., Grand Island, N.Y.) and diluted to appropriate concentrations. Bacterial biofilms were grown on premade polymethylmethacrylate (PMMA) disks 22 mm in diameter and 4 mm thick by the following method:

Sterile PMMA disks were placed into 100 ml erlenmeyer flasks containing 80 ml of sterile TSB. The flasks were inoculated with log phase bacteria and incubated on an orbital shaker (250 rpm) for 72 hours at 34° C. Every 24 hours, the old media was removed and replaced with 80 ml of sterile TSB. After 72 hours, the biofilm containing PMMA disks were removed using aseptic techniques and washed twice in PBS to remove nonadherent bacteria. The washed PMMA disks were placed in sterile PBS at 4° C. until needed. Planktonic bacteria were quantitated by standard dilution agar plating techniques. Biofilm bacteria were quantitated by sonication of the PMMA disks at 3000 cycles/second for 5 minutes on a sonifer commercially available as a "Bronson Sonifer 450®" from Bronson Ultrasonic Corp., Danbury, Conn., to remove adherent bacteria and standard dilution agar plating techniques were used to quantify biofilm bacteria.

Antimicrobials

The antibiotics used were: Penicillin G and Kanamycin A monosulfate, both commercially available from Sigma Chemical Co. Antibiotic solutions were freshly made before each assay and diluted in sterile PBS and modified PBS buffers.

Electric Equipment

Bacteria, planktonic and biofilm, were exposed to an electric field generated by low voltage electric currents in polystyrene disposable 50 ml conical tubes disposed in the device depicted in FIG. 3. Two platinum electrodes (1 cm×5 cm) were connected to a direct current power supply (0–20 volts, 0–3 amps) and an amp meter. Various currents ranging from 1–50 milliamps (ma) were used. Polarity, at 3 duty cycles per hour, was switched manually.

In the following Examples, the effect of electric fields on planktonic and biofilm bacteria was assessed by inoculating 10 ml of the buffer (with or without antibiotic) solution with a known concentration of planktonic bacteria or biofilm contaminated PMMA disk. The electrodes were placed in the suspension and current was applied. After the exposure time, the surviving bacteria were quantitated as described above.

Example 1

In this Example, the effects of exposing planktonic and biofilm bacteria to various alternating current was measured. Samples of planktonic bacteria (*Escherichia coli* ATCC#8739 and *Staphylococcus epidermidis* ATCC#12228) and biofilm bacteria (*Staphylococcus epidermidis* ATCC#35984 and *Escherichia coli* ATCC#15221) in PBS were exposed to electric currents ranging from 0–50 milliamps, at 3 duty cycle per hour, for one hour. Both the planktonic and biofilm bacteria were present in concentrations of $10^6$ CFU/ml. Survival of bacteria was determined as described above. The results are reported in Table 1.

TABLE 1

Effect of various electric fields on planktonic and biofilm bacteria after one hour exposure in unmodified phosphate buffered saline

| | Log Number Survival After Exposure | | | |
|---|---|---|---|---|
| | Planktonic | | Biofilm | |
| Exposure Conditions (ma) | S. epid #12228 | E. coli #3739 | S. epid #35984 | E. coli #15221 |
| 0 | 6 | 6 | 6 | 6 |
| 1 | 6 | 6 | 6 | 6 |
| 2 | 5 | 5 | 6 | 6 |
| 5 | 3 | 3 | 4 | 4 |
| 10 | 0 | 0 | 4 | 3 |
| 20 | 0 | 0 | 2 | 2 |
| 30 | 0 | 0 | 0 | 0 |
| 40 | 0 | 0 | 0 | 0 |
| 50 | 0 | 0 | 0 | 0 |

The results in Table 1 demonstrate that electric fields alone at various levels can eradicate planktonic and biofilm bacteria. The minimum electric field to completely eradicate planktonic bacteria was generated by a current of 10 milliamps. The minimum electric field to completely eradicate biofilm bacteria was generated by a current of 30 milliamps.

Example 2

Previous studies (Shimada (1982); Pareilleux; Hamilton) have shown that exposing planktonic bacteria in an aqueous suspension to electric field can cause complete eradication of the bacteria. This lethal effect is believed to be due to electrolytically generated in situ biocides such as active chlorine, free radicals, and heavy metal ions. This example illustrates the results of the addition of a neutralizer to the aqueous solution to neutralize the in situ biocides which are generated.

One hundred milliliters of PBS was modified by adding 1.6 g of sodium thiosulfate and 10,000 units of bovine liver catalase (commercially available from Sigma Chemical Co.). A suspension of planktonic *Escherichia coli* ATCC 8739 and *Staphylococcus epidermidis* ATCC#12228, in concentrations of $10^6$ CFU/ml, were exposed in modified PBS to an electric field generated by 20 milliamps for 8 hours. Survival of bacteria was determined as described above. The results are reported in Table 2.

TABLE 2

Effect of 20 ma electric field on planktonic bacteria after 8 hours exposure in modified phosphate buffered saline

| Exposure Time | Log Number Survival After Exposure | |
|---|---|---|
| (Hours) | S. epid #12223 | E. coli #8739 |
| 0 | 6 | 6 |
| 1 | 6 | 6 |
| 2 | 6 | 6 |
| 3 | 6 | 6 |
| 4 | 6 | 6 |
| 5 | 6 | 6 |
| 6 | 5 | 5 |
| 7 | 5 | 5 |
| 8 | 5 | 5 |

Example 1 demonstrated that exposure of planktonic bacteria in PBS to an electric field generated by an electric current of 20 milliamps at 3 duty cycles per hour can cause complete eradication of bacteria within one hour. The results of this Example demonstrate that the electrolytically generated biocides can be effectively neutralized by the addition of sodium thiosulfate and bovine liver catalase (Table 2). With the in situ generated biocides neutralized, the true synergistic effects of various electric fields and antibiotic can be observed.

Example 3

In this Example, the effects of exposing biofilm bacteria to penicillin G and to electric fields generated by low alternating current were measured. Samples of biofilm bacteria (*Escherichia coli* ATCC#15221 and *Staphylococcus epidermis* ATCC#35984) in PBS, modified as in Example 2, and grown on PMMA disks were exposed to 25 to 25000 units/ml of penicillin G in combination with an electric field generated by electric current at 10, 15, and 20 milliamps at 3 duty cycle per hour, for 8 hours. Survival of bacteria was determined as in Example 1. "PBS Control" contained biofilm bacteria in modified PBS, but was not exposed to biocide nor to an electric field. The results in Table 3 demonstrate that there is synergistic enhancement of the antibiotics activity against these biofilm bacteria when combined with various electric fields generated by electric currents. The enhanced kill of the combined treatment can be postulated to be due to enhancement of the antibiotic penetration, and not the generation of other biocides in the buffer, since, as shown in Example 2, the modified PBS effectively neutralizes any electrolytically generated biocides.

TABLE 3

Effect of various electric fields with Penicillin G on *Escherichia coli* #15221 & *Staphylococcus epidermidis* #35984 Biofilms after 8 hours exposure

| Exposure Conditions (current and/or antimicrobial concentration) | Log Number Survival After Exposure | |
|---|---|---|
| | E. coli | S. epid. |
| *Electric Field Alone* | | |
| PBS Control | 6 | 6 |
| 10 ma | 6 | 6 |
| 15 ma | 6 | 6 |
| 20 ma | 5 | 6 |
| *Biocide Alone* | | |
| 25 units/ml | 6 | 6 |
| 250 units/ml | 6 | 6 |
| 2500 units/ml | 6 | 6 |
| 250000 units/ml | 6 | 6 |
| *Electric Field and Biocide* | | |
| 10 ma & 25 units/ml | 6 | 6 |
| 10 ma & 250 units/ml | 6 | 6 |
| 10 ma & 2500 units/ml | 5 | 6 |
| 10 ma & 25000 units/ml | 4 | 6 |
| 15 ma & 25 units/ml | 6 | 6 |
| 15 ma & 250 units/ml | 6 | 6 |
| 15 ma & 2500 units/ml | 4 | 6 |
| 15 ma & 25000 units/ml | 3 | 5 |
| 20 ma & 25 units/ml | 5 | 5 |
| 20 ma & 250 units/ml | 5 | 5 |
| 20 ma & 2500 units/ml | 4 | 5 |
| 20 ma & 25000 units/ml | 0 | 4 |

TABLE 4

Effect of various electric fields with Kanamycin A Monosulfate on *Escherichia coli* #15221 & *Staphylococcus epidermidis* #35984 Biofilms after 8 hours of exposure

| Exposure Conditions (current and/or antimicrobial concentration) | Log Number Survival After Exposure | |
|---|---|---|
| | E. coli | S. epid. |
| *Electric Field Alone* | | |
| PBS Control | 6 | 6 |
| 10 ma | 6 | 6 |
| 15 ma | 6 | 6 |
| 20 ma | 5 | 6 |
| *Biocide Alone* | | |
| 0.25 ug/ml | 6 | 6 |
| 2.5 ug/ml | 6 | 6 |
| 25 ug/ml | 6 | 6 |
| 250 ug/ml | 6 | 5 |
| *Electric Field and Biocide* | | |
| 10 ma & 0.25 ug/ml | 6 | 6 |
| 10 ma & 2.5 ug/ml | 5 | 5 |
| 10 ma & 25 ug/ml | 4 | 4 |
| 10 ma & 250 ug/ml | 0 | 3 |
| 15 ma & 0.25 ug/ml | 6 | 6 |
| 15 ma & 2.5 ug/ml | 5 | 5 |
| 15 ma & 25 ug/ml | 3 | 3 |
| 15 ma & 250 ug/ml | 0 | 0 |
| 20 ma & 0.25 ug/ml | 5 | 5 |
| 20 ma & 2.5 ug/ml | 4 | 5 |
| 20 ma & 25 ug/ml | 3 | 2 |
| 20 ma & 250 ug/ml | 0 | 0 |

Example 4

In this Example, the effects of exposing biofilm bacteria to Kanamycin A monosulfate and to electric fields generated by low alternating current were demonstrated. Samples of biofilm bacteria (*Escherichia coli* ATCC#15221 and *Staphylococcus epidermis* ATCC#35984) in PBS, modified as in Example 2, and grown on PMMA disks were exposed to 0.25, 2.5, 25, and 250 g/ml of Kanamycin A monosulfate in combination with an electric field generated by electric current at 10, 15, and 20 milliamps at 3 duty cycle per hour, for 8 hours. Survival of bacteria was determined as in Example 1. "PBS Control" contained biofilm bacteria in modified PBS, but was not exposed to biocide nor to an electric field. The results in Table 4 demonstrate that there is synergistic enhancement of the antibiotics activity against biofilm bacteria when combined with an electric field generated by electric current. Again, the enhanced kill of the combined treatment can be postulated to be due to enhancement of the antibiotic penetration, and not the generation of other biocides in the buffer.

Example 5

In this Example, the effect of exposing a modified liquid sterilant inoculated with a bacterial spore suspension to electric fields generated by alternating current was measured.

The liquid sterilant used was "Glutarex™ Disinfecting and Sterilizing Solution", commercially available from 3M, St. Paul, Minn. For each assay, a fresh 2 quart bottle was activated. The liquid sterilant was modified by adding 0.85 w/v % sodium chloride, 1.6 w/v % sodium thiosulfate, and 10,000 units/100 ml of catalase, to neutralize any electrolytically generated biocide, so that the effect of electric field upon the effectiveness of the sterilant could be observed.

The bacterial spore suspension was prepared by: 1) inoculating sterile TSB with *Bacillus subtilis* var. *Niger spores* ATCC#9732, commercially available from American Type Culture Collection; 2) incubating the spores for 24 hours at 37° C. to produce cells; 3) pelletizing the cells by centrifugation at 6000 rpms for 30 minutes and washing twice in sterile distilled water; 4) making agar plates by mixing 40 g of nutrient broth agar with 0.5 g of manganese sulfate, aseptically pouring 85 ml of liquid agar mixture prepared according to the specifications of the manufacturer, Difco Laboratories Inc., onto sterile 150 mm polystyrene petri dishes, and allowing the agar to solidify; 5) inoculating the plates with the *Bacillus subtilis* cells prepared in steps 1–3; 6) incubating the plates for 6 days at 37° C.; 7) removing the spore cells and washing the cells twice in sterile distilled water; 8) quantitating the spores using tryptic soy agar (TSA), commercially available from Difco Laboratories, Inc., and standard dilution plating techniques; and 9) making a suspension of the *B. subtilis* spores at the concentration of $2 \times 10^{10}$ colony forming units (CFU)/ml in sterile distilled water.

The assessment of enhancement of sporicidal activity by exposure to an electric field generated by alternating current was determined by the following assay: Two 10 mls aliquots of the modified liquid sterilant were inoculated with $10^8$ of the *B. subtilis* spores. After mixing for about 15 seconds, a 1 ml aliquot was removed from each suspension and quickly neutralized by placing it in a 9 ml PBS, modified as in Example 2. This was the "0" time control for each suspension. Of the remaining liquid sterilant/spore suspensions one was mixed on an orbital shaker and the other was placed in the test device described above and depicted in FIG. 3, and exposed to an electric field generated by 20 ma of electric current at 3 duty cycles per hour. Aliquots (1 ml) of both suspensions were removed and neutralized in PBS 9 mls of modified as in Example 2, at each of the various time periods, 15, 30, 60, 90, 120, and 180 minutes. Following exposure and neutralization, 1 ml aliquots were plated out using TSA. Plates were incubated at 34° C., and growth (+) or no growth (−) was visually observed at 24, 48, and 72 hours. The results are reported in Table 5.

TABLE 5

Effects of alternating current on sporicidal activity of "Glutarex ™ Disinfecting and Sterilizing Solution"

| Exposure Time | Exposed to Sterilant Outgrowth at | | | Exposed to Sterilant and 20 ma Outgrowth at | | |
|---|---|---|---|---|---|---|
| (min.) | 24 hr | 48 hr | 72 hr | 24 hr | 48 hr | 72 hr |
| 0 | + | + | + | + | + | + |
| 15 | + | + | + | + | + | + |
| 30 | + | + | + | − | + | + |
| 60 | + | + | + | − | − | − |
| 90 | + | + | + | − | − | − |
| 120 | − | + | + | − | − | − |
| 180 | − | − | + | − | − | − |

A 2% solution of glutaraldehyde, ("Glutarex™ Disinfecting and Sterilizing Solution") has been shown to kill spores within 3 hours. Seymour S. Block, *Disinfection, Sterilization and Presentation,* 4th Edition, Lea and Fetiger, Philadelphia London, 1991 (p. 599). The results in Table 5 demonstrate that an electric field generated by alternating current enhances the sterilant activity of "Glutarex™ Disinfecting and Sterilizing Solution" against *B. subtilis* suspensions. When exposed to an electric field and "Glutarex™ Disinfecting and Sterilizing Solution", the spores were completely killed after a 30 minute exposure time as compared to more than 180 minute exposure time for the control.

Example 6

In this Example, the effects of exposing *B. subtilis* biofilm contaminated suture loops in a modified liquid sterilant to electric fields generated by alternating current was measured.

The liquid sterilant used was as described in Example 5. Suture loops were prepared from a spool of size 3 suture commercially available as "Silk Black Braid A-59" from Ethicon, Inc., Somerville, N.J., by wrapping the silk suture around an ordinary pencil 4 times, slipping the coil off the end of the pencil, and passing another piece of suture through the coil, knotting and tying securely. The suture loops were sterilized by placing them in 0.5N HCl for 15 minutes. The acid solution was decanted off, and the loops rinsed 4 times with 100 ml of sterile distilled water. The sterile loops were contaminated by placing them in solution of PBS inoculated with $10^7$ spores/ml using the suspension of *B. subtilis* spores prepared according to Example 5. The loop suspensions were agitated for one minute and incubated at room temperature for 15 minutes. The contaminated suture loops were removed and placed in a sterile petri dish and dried by vacuum at 69 cm Hg for 2 days.

The assessment of enhancement of sporicidal activity in an electric field generated by alternating current was accomplished by the following assay: Two contaminated suture loops were added to several 10 ml aliquots of modified liquid sterilant. Two loops from one of the 10 ml suspensions were removed and quickly neutralized in PBS modified as in Example 2. This was the "0" time control. The remaining suspensions were either exposed to an electric field generated by 20 ma of electric current at 3 duty cycles per hour or placed on an orbital shaker. Two suture loops were removed and neutralized in modified PBS at each of the time intervals, 60, 120, 180, 240, and 300 minutes. The neutralized loops were plated out in TSA and growth (+) or no growth (−) was visually observed at 24, 48, and 72 hours. The results are reported in Table 6.

TABLE 6

Effects of alternating current on sporicidal activity of "Glutarex ™ Disinfecting and Sterilizing Solution" (using vacuum dried contaminated suture loops)

| Exposure Time | Exposed to Sterilant Outgrowth at | | | Exposed to Sterilant and 20 ma Outgrowth at | | |
|---|---|---|---|---|---|---|
| (min.) | 24 hr | 48 hr | 72 hr | 24 hr | 48 hr | 72 hr |
| 0 | + | + | + | + | + | + |
| 60 | + | + | + | − | − | − |
| 120 | + | + | + | − | − | − |
| 180 | + | + | + | − | − | − |
| 240 | − | + | + | − | − | − |
| 300 | − | − | ? | − | − | − |

According to the Association of Official Analytical Chemists (AOAC), *B. subtilis* spores vacuum dried on suture loops are highly resistant to glutaraldehyde based sterilants. "Official Methods of Analysis of the Association of Official Analytical Chemists", 15th Edition (1990), edited by Kenneth Helrich, published by AOAC, Inc., Suite 400, 2200 Wilson Blvd., Arlington, Va. In fact 10 hours of exposure to 2% glutaraldehyde are required to kill *B. subtilis* spores vacuum dried on suture loops. "Official Methods of Analysis of the Association of Official Analytical Chemists", supra The results in Table 6 demonstrate that exposing a contaminated suture loop to an electric field generated by 20 ma alternating electric current and modified "Glutarex™ Disinfecting and Sterilizing Solution" enhance the sporicidal activity of the liquid sterilant. The *B. subtilis* spores vacuum dried on suture loops were eradicated after a 60 minute exposure time in liquid sterilant to an electric field generated by electric current, as compared to more than a 240 minute exposure time for the liquid sterilant control.

Example 7

In this Example, the effects of exposing *B. subtilis* biofilm contaminated suture loops in a modified liquid sterilant and 5% fetal calf serum (FCS) to an electric field generated by alternating current was measured. The presence of serum protein provided a greater challenge to the combination of liquid sterilant and exposure to an electric field generated by electric current.

The liquid sterilant used was as described in Example 5. Suture loops were prepared as described in Example 6 except they were contaminated by placing them in solution of PBS with 5% fetal calf serum (commercially available from Gibco Lab, Life Technologies, Inc., Grand Island, N.Y.) inoculated with $10^7$ spores/ml. The loop suspensions were agitated for one minute and incubated at room temperature for 15 minutes. The contaminated suture loops were removed and placed in a sterile petri dish and dried by vacuum at 69 cm Hg for 2 days.

The assessment of enhancement of sporicidal activity by exposure to an electric field generated by alternating current was accomplished by the following assay: Two contaminated suture loops were added to several 10 ml aliquots of modified liquid sterilant. Two loops from one of the 10 ml suspensions were removed and quickly neutralized in modified PBS. This was the "0" time control. The remaining suspensions were either exposed to an electric field generated by 20 ma of electric current at 3 duty cycles per hour or placed on an orbital shaker. Two suture loops were removed and neutralized in modified PBS at each of the time intervals, 60, 120, 180, 240, and 300 minutes. The neutralized loops were plated out in TSA and growth (+) or no growth (−) was visually observed at 24, 48, and 72 hours. The results are reported in Table 7.

TABLE 7

Effects of alternating current on sporicidal activity of "Glutarex ™ Disinfecting and Sterilizing Solution" (using vacuum dried contaminated suture loops with FCS)

| Exposure Time | Exposed to Sterilant Outgrowth at | | | Exposed to Sterilant and 20 ma Outgrowth at | | |
|---|---|---|---|---|---|---|
| (min.) | 24 hr | 48 hr | 72 hr | 24 hr | 48 hr | 72 hr |
| 0 | + | + | + | + | + | + |
| 60 | + | + | + | − | − | + |
| 120 | + | + | + | − | − | − |
| 180 | + | + | + | − | − | − |
| 240 | + | + | + | − | − | − |
| 300 | + | + | + | − | − | − |

The results in Table 7 demonstrate that exposing a contaminated suture loop to an electric field generated by 20 ma alternating electric current in modified "Glutarex™ Disinfecting and Sterilizing Solution" enhances the sporicidal activity of the liquid sterilant. The *B. subtilis* spores on the suture loops were eradicated after a 120 minute exposure time to an electric field generated by electric current in liquid sterilant, as compared to more than 300 minute exposure time for the liquid sterilant control.

I claim:

1. A method of killing microorganisms in a biofilm comprising applying an electric field to an electrically conductive medium in which the biofilm is contained, no portion of the source of electric field being in contact with the biofilm and the strength of the electric field and the duration of application being sufficient to produce killing of microorganisms in the biofilm.

2. The method of claim 1 wherein said electrically conductive medium contains no added biocide, but is capable of generating in situ an effective amount of a biocide upon application of said electric field.

3. The method of claim 2 wherein said electrically conductive medium is capable of generating a biocidally effective amount of an active chlorine, superoxide, free radical, heavy metal ion, or a combination thereof.

4. The method of claim 2 wherein said biocide generated is present in a concentration of 1 ng/ml to 1 g/ml.

5. The method of claim 1 wherein said electrically conductive medium comprises an effective amount of a biocide additive.

6. The method of claim 5 wherein the biofilm is composed predominately of bacteria, yeast, fungus or mold and said biocide is an antibiotic; an antifungal agent; or a disinfectant or sterilant selected from the group consisting of active chlorine, quaternary ammonium compounds, heavy metals, peroxides and aldehydes.

7. The method of claim 5, wherein the biofilm is composed predominately of bacteria, and said biocide is an antibiotic selected from the family of antibiotics consisting of penicillins, cephalosporins, aminoglycosides, tetracyclines, sulfonamides, macrolide antibiotics and quinolones.

8. The method of claim 5 wherein said biocide additive is present in a concentration of 1 ng/ml to 1 g/ml.

9. The method of claim 1 wherein said electrically conductive medium is a buffered saline solution.

10. The method of claim 1, wherein said electric field is substantially constant.

11. The method of claim 1, wherein said electrical field is a pulsed or alternating electric field.

12. The method of claim 1, wherein said electric field strength is generated by currents of between 1 and 200 milliamps.

13. The method of claim 1, wherein said electric field is applied to the electrically conductive medium for a period of time of between 1 minute and 48 hours.

14. The method of claim 1 wherein said medium comprises a biocide in an amount which would be ineffective to completely kill the biofilm microorganisms if used in the absence of an electric field.

15. The method of claim 1 wherein said biofilm is contained in a living subject and exposed to internal body fluids which comprise the electrically conductive medium, and said electric field is generated by a noninvasive electric field generating device.

16. A method of killing microorganisms which form a biofilm on a surface exposed to internal body fluids in a living subject, comprising a) administering an effective amount of a biocide to the subject for a period of time; and b) during at least a portion of said period of time exposing said biofilm to an electric field whose field strength and duration are sufficient to produce killing of said microorganism in said biofilm, said electric field having generated by a noninvasive electric field generating device.

17. The method of claim 16, wherein the biofilm is composed predominately of bacteria, and said biocide is an antibiotic selected from the family of antibiotics consisting of penicillins, cephalosporins, aminoglycosides, tetracyclines, sulfonamides, macrolide antibiotics and quinolones.

18. The method of claim 16 wherein said biocide is present in an amount which would be ineffective to completely kill the biofilm microorganisms if used in the absence of an electric field.

19. The method of claim 18 wherein said sterilant or disinfectant is selected from the group consisting of active chlorines, quaternary ammonium compounds, heavy metals, peroxides and aldehydes.

20. The method of claim 18 wherein said sterilant or disinfectant is present in an amount which would be ineffective to produce complete killing of the biofilm microorganisms if used in the absence of an electric field.

21. A method of killing microorganisms in a biofilm comprising placing an article contaminated with a biofilm in an electrically conductive medium and applying an electric field to said medium with no portion of the source of electric field being in contact with the biofilm the strength of said electric field and the duration of application being sufficient to produce killing of said microorganisms in said biofilm.

22. A method of sterilizing articles which may be contaminated by a biofilm comprising:
   a) placing the article in an electrically conductive medium which contains an effective amount of a sterilant or disinfectant; and
   b) passing an electric field through the medium, no portion of the source of electric field being in contact with the biofilm and the strength of the electric field and the duration of application being sufficient to produce killing of the microorganisms in the biofilm.

23. A method of disinfecting articles which may be contaminated by a biofilm comprising:
   a) placing the article in an electrically conductive medium which contains an effective amount of a sterilant or disinfectant; and
   b) passing an electric field through the medium, no portion of the source of electric field being in contact with the biofilm and the strength of the electric field and the duration of application being sufficient to produce killing of the microorganisms in the biofilm.

* * * * *

UNITED STATES PATENT AND TRADEMARK OFFICE
CERTIFICATE OF CORRECTION

PATENT NO.: 5,462,644

DATED: October 31, 1995

INVENTOR(S): Woodson

It is certified that error appears in the above-identified patent and that said Letters Patent is hereby corrected as shown below:

Col. 9, line 42    "pH 5.07.4" should be --pH 5.0-7.4--

Col. 13, line 46   "250 g/ml" should be --250 µg/ml--

Signed and Sealed this

Twenty-second Day of April, 1997

Attest:

BRUCE LEHMAN

Attesting Officer

Commissioner of Patents and Trademarks